US007372059B2

(12) United States Patent
Shumlak et al.

(10) Patent No.: US 7,372,059 B2
(45) Date of Patent: May 13, 2008

(54) PLASMA-BASED EUV LIGHT SOURCE

(75) Inventors: Uri Shumlak, Seattle, WA (US); Raymond Golingo, Seattle, WA (US); Brian A. Nelson, Mountlake Terrace, WA (US)

(73) Assignee: The University of Washington, Seattle, WA (US)

( * ) Notice: Subject to any disclaimer, the term of this patent is extended or adjusted under 35 U.S.C. 154(b) by 389 days.

(21) Appl. No.: 11/252,021

(22) Filed: Oct. 17, 2005

(65) Prior Publication Data

US 2007/0085042 A1 Apr. 19, 2007

(51) Int. Cl.
*A61N 5/06* (2006.01)
*G01J 3/10* (2006.01)
*H05G 2/00* (2006.01)

(52) U.S. Cl. ............................. 250/504 R; 250/505.1; 250/493.1; 378/119; 378/121; 378/122; 378/145; 378/34; 378/84; 315/111.31; 315/111.41; 315/111.81; 315/111.91; 219/121.31; 219/121.41; 219/121.48; 313/231.31; 313/231.41

(58) Field of Classification Search ............ 250/504 R, 250/505.1, 493.1; 378/119, 121, 122, 145, 378/34, 84; 315/111.31, 111.41, 111.81, 315/111.91; 219/121.31, 121.41, 121.48; 313/231.31, 213.41
See application file for complete search history.

(56) References Cited

U.S. PATENT DOCUMENTS 6,566,667 B1 * 5/2003 Partlo et al. ............ 250/504 R
6,804,327 B2 * 10/2004 Schriever et al. ........... 378/119
6,894,298 B2 * 5/2005 Ahmad et al. .......... 250/504 R

OTHER PUBLICATIONS

Arber, T. D. et al., "The effect of sheared axial flow on the linear stability of the Z-pinch," *Phys. Plasmas*, Feb. 1996, 3(2), 554-560.

Banine, V. et al., "EUV lithography: Main challenges," *Micro- and Nanoelectronics*, 2004, 5401, 1-7.

Borisov, V. M. et al., "EUV sources using Xe and Sn discharge plasmas," *J. Phys. D: Appl. Phys.*, 2004, 37, 3254-3265.

Brown, K. H., "In the End It's the Bottom Lin That Counts," *Proceedings of SPIE*, 2004, 5374, 9-15.

(Continued)

*Primary Examiner*—Jack Berman
*Assistant Examiner*—Meenakshi S Sahu
(74) *Attorney, Agent, or Firm*—Woodcock Washburn LLP

(57) ABSTRACT

Various mechanisms are provided relating to plasma-based light source that may be used for lithography as well as other applications. For example, a device is disclosed for producing extreme ultraviolet (EUV) light based on a sheared plasma flow. The device can produce a plasma pinch that can last several orders of magnitude longer than what is typically sustained in a Z-pinch, thus enabling the device to provide more power output than what has been hitherto predicted in theory or attained in practice. Such power output may be used in a lithography system for manufacturing integrated circuits, enabling the use of EUV wavelengths on the order of about 13.5 nm. Lastly, the process of manufacturing such a plasma pinch is discussed, where the process includes providing a sheared flow of plasma in order to stabilize it for long periods of time.

20 Claims, 10 Drawing Sheets

OTHER PUBLICATIONS

Chapman, B. E. et al., "Strong E x B Flow Shear and Reduced Fluctuations in a Reversed-Field Pinch," *Physical Review Letters*, Mar. 9, 1998, 80(10), 2137-2140.

Chu, M. S. et al., "Effect of toroidal plasma flow and flow shear on global magnetohydrodynamic MHD modes," *Phys. Plasmas*, Jun. 1995, 2(6), 2236-2241.

Fomenkov, I. V. et al., "EUV discharge light source based on a dense plasma focus operated with positive and negative polarity," *J. Phys. D: Appl Phys.*, 2004, 37, 3266-3276.

Golingo, R. P. et al., "Formation of a sheared flow Z pinch," *Physics of Plasmas*, 2005, 12, 062505-1-9.

Golingo, R. P. et al., "Spatial deconvolution technique to obtain velocity profiles from chord integrated spectra," *Review Of Scientific Instruments*, Apr. 2003, 74(4), 2332-2337.

Greenwood, J. R. et al., "Xenon re-circulation systems for next generation lithography tools," *Proceedings of SPIE*, 2004, 5374, 991-997.

Kieft, E. R. et al., "Characterization of a vacuum-arc discharge in tin vapor using time-resolved plasma imaging and extreme ultraviolet spectrometry," *Physical Review E*, 2005, 71, 026409-1-7.

Kieft, E. R. et al., "Comparison of experimental and simulated extreme ultraviolet spectra of xenon and tin discharges," *Physical Review E*, 2005, 71, 036402-1-12.

McGeoch, M., "Pinch plasma EUV source with particle injection," *J. Phys. D: Appl. Phys.*, 2004, 37, 3277-3284.

Meiling, H. et al, "Progress in the ASML EUV program," *Proceedings of SPIE*, 2004, 5374, 31-42.

Miller, R. L. et al., "Stabilization of ballooning modes with sheared toroidal rotation," *Phys. Plasmas*, Oct. 1995, 2(10), 3676-3684.

Nastoyashchii, A. F., "Optimal physical conditions for extreme UV generation," *Proceedings of SPIE*, 2004, 5448, 749-755.

Pankert, J. et al., "Physical Properties of the HCT EUV Source," *Proceedings of SPIE*, 2003, 5037, 112-118.

Sasaki, A. et al., "Simulation of the EUV Spectrum of XE and Sn Plasmas," *IEEE Journal of Selected Topics in Quantum Electronics*, Nov./Dec. 2004, 10(6), 1307-1314.

Shumlak, U. et al., "Evidence of Stabilization in the Z-Pinch," *Physical Review Letters*, Nov. 12, 2001, 87(20), 205005-1-4.

Shumlak, U. et al., "Sheared Flow Stabilization of the m=1 Kink Mode in Z Pinches," *Physical Review Letters*, Oct. 30, 1995, 75(18), 3285-3288.

Shumlak, U. et al., "Sheared flow stabilization experiments in the ZaP flow Z pinch," *Physics of Plasmas*, May 2003, 10(5), 1683-1690.

Silverman, P. J., "Extreme ultraviolet lithography: overview and development status," *J. Microlith, Microfab, Microsyst.*, Jan.-Mar. 2005, 4(1), 011006-1-5.

Stamm, U., "Extreme ultraviolet light sources for use in semiconductor lithography—state of the art and future development," *J. Phys. D: Appl. Phys.*, 2004, 37, 3244-3253.

Stamm, U. et al., "High Power EUV Lithography Sources Based on Gas Discharges and Laser Produced Plasmas," *Proceedings of SPIE*, 2003, 5037, 119-129.

Teramoto, Y. et al., "Development of Xe-filled capillary discharge extreme ultraviolet radiation source for semiconductor lithography," *Proceedings of SPIE*, 2003, 5037, 767-775.

Teramoto, Y. et al., "High repetition rate MPC generator-driven capillary Z-pinch EUV source," *Proceedings of SPIE*, 2004, 5374, 935-942.

* cited by examiner

PLASMA-BASED EUV LIGHT SOURCE

STATEMENT OF GOVERNMENT SUPPORT

This invention was made by government support by U.S. Department of Energy Grant No. DE-FG03-98-ER54460. The Government has certain rights in this invention.

TECHNICAL FIELD

The presently disclosed subject matter relates to the providing of a plasma-based extreme ultraviolet (EUV) light source. More specifically, it relates to the applicability of such a light source in, for example, lithography.

BACKGROUND

Lithography is used in the manufacture of integrated circuits. It is used to transfer circuit patterns from a mask to silicon (or other equivalent and alternative) surfaces. In recent times, for optical lithography at least, the characteristic wavelength has decreased from 365 nm (nanometers) to 248 nm to 193 nm and is currently migrating to 157 nm. At a 157 nm wavelength, for example, features could be printed at a resolution of 100 nm and maybe even at a 70 nm level using phase-shift masks and optical proximity correction.

EUV light can further extend optical lithography by using wavelengths in the range of 11 to 14 nm, allowing for shrinkage of feature size. For example, a 13.5 nm EUV system could theoretically print features much less than 30 nm. Operation at such extremely short wavelengths, presents a number of problems. Some of these problems have to do with optical absorption, requiring the use of reflective materials instead of refractive ones; others have to do with optical contamination, requiring a vacuum environment. Still other problems arise in power production, where an EUV source cannot produce but a fraction of the suggested manufacturing power output, which may be on the order of at least 100 watts of power at the entrance of the optics system or intermediate focus. To solve at least the last of these problems, it would be advantageous to provide various plasma-based EUV light source mechanisms, where, for example, the desired EUV wavelength could be used at a desired power output level in, for example, lithography.

SUMMARY

In response to the problems and needs presented above, plasma-based EUV light source mechanisms are provided suitable for use in integrated circuit lithography. In one aspect of the presently disclosed subject matter, a manner of producing EUV light is provided, where a neutral gas can be ionized into a plasma, and the plasma can be accelerated to produce a sheared, non-uniform, plasma flow. Based on the sheared plasma flow, a plasma pinch can be formed for an extended period of time, typically several orders of magnitude longer than anything that has been done hitherto in the art. Such prolonged plasma sustenance, which may be a function of the sheared plasma flow formation into the plasma pinch, allows corresponding magnified EUV power output. Large power output, in turn, can be used in optical lithography for integrated circuit manufacture.

As for the types of plasma used for the EUV generation, such elements as Xenon, Tin, or Lithium may be used. Using sheared flow of such plasma may allow a significantly increased time sustenance of the pinch, ranging anywhere from 20 to 40 microseconds (μs). Such extensive temporal pinch sustenance may emit light with wavelengths in a range around 13.5 nm with enough power to deliver at least 100 watts to an intermediate focus of a lithography optics system—even at a lower duty cycle than traditional equivalent mechanisms. However, this EUV generation process may be repeated at a duty cycle in the kilohertz (kHz) range, if so desired—but is not strictly required, given the amount of power generated by the plasma pinch.

Moreover, various types of apparatuses or devices may be used to accomplish such EUV generation. For example, one such apparatus may have a first electrode coaxially arranged with a second electrode, where the first electrode may be an anode and the second electrode may be a cathode (or vice versa). A plasma pinch may be formed in the interstice of the electrodes, with the aid of voltages and magnetic fields. Furthermore, various ports and injection valves may be provided. For example, a valve for injecting a neutral gas (or a pre-ionized plasma) into the interstice may used, and ports can be used to observe, measure, and record a set of events associated with the plasma.

Lastly, this apparatus can be arranged in an EUV system suitable for lithography, where the plasma pinch may act as a light source, thus enabling integrated circuit manufacture in conjunction with masks, optical condensers and projections, and silicon or other wafers. It should be noted, that this Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The foregoing Summary, as well as the following Detailed Description, is better understood when read in conjunction with the appended drawings. In order to illustrate the present disclosure, various aspects of the disclosure are shown. However, the disclosure is not limited to the specific aspects discussed. The following figures are included.

DETAILED DESCRIPTION

Various aspects of the subject matter illustrated in FIGS. 1A-4 are described in more detail directly below. First, general aspects of a device configured to produce sheared plasma flow are considered, followed by a discussion of an exemplary process or method of producing EUV light based on such sheared plasma flow. Lastly, a system for using such EUV light is considered, where the system is used in lithography.

Aspects of Light Source Configured for Producing EUV Light

Figure 1A:
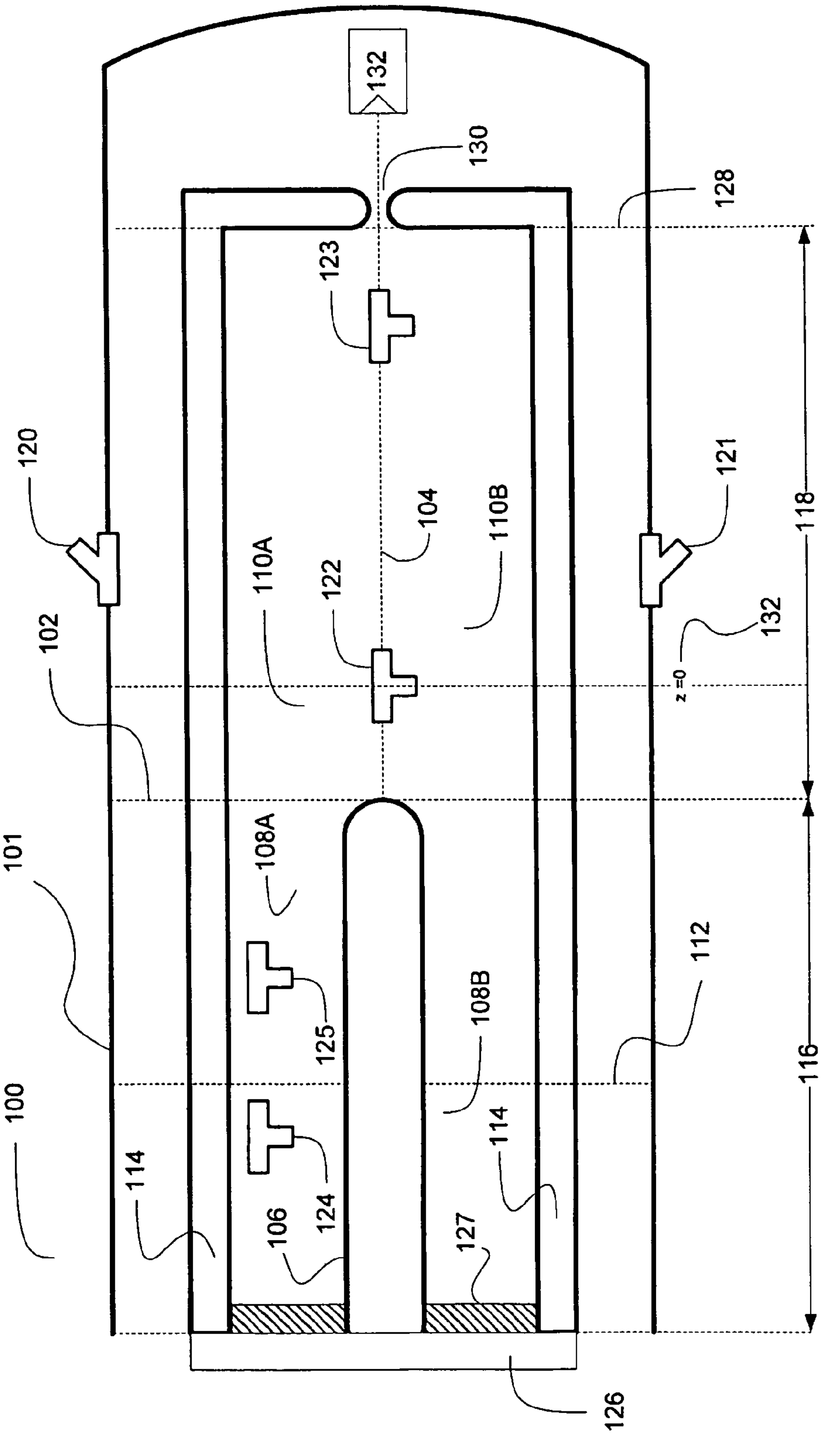
FIG. 1A illustrates one device which may be implemented in producing sheared plasma flow in order to provide an EUV light source.

Various mechanisms may be used for producing EUV Light. In one aspect of the presently disclosed subject matter, a “Z-pinch” 100 is shown in FIG. 1A. The Z-pinch 100 is a type of plasma confinement system that relies on the Lorentz force to “pinch” or compress the plasma to high temperatures. For example, such a confinement system 100 may be a vacuum vessel 101 that contains the plasma.

According to FIG. 1A, the Z-pinch 100 may comprise of two regions: an acceleration region 116 and an assembly region 118. As will be explained below in greater detail, plasma in the Z-pinch 100 may start out in the acceleration region 116 and become pinched in the assembly region 118. The line of demarcation 102 between these regions is, of course, merely a conceptual line, and is shown as a dashed line 102. It should be noted, moreover, that the term “Z-pinch” is used loosely here, since, technically speaking, the “Z-pinch” may also be understood to extend from the dashed demarcation line 102 to the end wall of the assembly region 128.

Furthermore, an axis of symmetry 104 may be shown around which the Z-pinch 100 may be constructed. Thus, the Z-pinch 100 may also comprise of two electrodes, which in turn may be an anode and a cathode. The first electrode may be an inner electrode 106 (shaded in gray color) and the second electrode may be an outer electrode 114 (also shaded in gray color). In one aspect of the presently disclosed subject matter, the arrangement of these electrodes may be coaxial in that one electrode surrounds the other around the mentioned axis of symmetry 104.

Furthermore, FIG. 1A shows an upper region 108A of the acceleration region 116 and a lower region 108B of the acceleration region 116. This distinction between the upper 108A and lower 108B region is, again, merely conceptual and is germane to the discussion of FIGS. 2A-2E, which focus only on the upper region 108A when discussing the acceleration region 116. This is done merely for brevity’s sake, and should not be interpreted as limiting in any way. Likewise, the assembly region 118 is also divided into an upper region 110A and a lower 110B region, and similarly, for brevity’s sake, only the upper region 110A is discussed in FIGS. 2A-2E.

The acceleration region 116 may be conceptually intersected by an injection plane 112, along which neutral gas may be injected into the Z-pinch 100. The neutral gas, upon ionization, becomes the aforementioned plasma. The injection plane 112 is shown using a dashed line, and corresponds to the port (not shown) via which the neutral gas is injected (the port or injection valve is shown in FIGS. 2A-2E). Notably, the injected gas does not have to be neutral, that is, it may already be in a plasma state, however, in this sample implementation of the presently disclosed subject matter, it is a neutral gas.

The Z-pinch 100 may have several different kinds of ports which may be used for measurement, observation, and equivalent purposes. By example only and not limitation, the Z-pinch 100 may have a top 120 and a bottom 121 port in the assembly region 118 which may be used for spectroscopic measurement of the contents of the Z-pinch 100. Similarly, the Z-pinch 100 may also have side ports, 122 and 123, which may be used for obtaining images from a fast framing camera and for measuring content density by interferometry. Also, smaller side ports 124 and 125 may be placed along the acceleration region 116 in order to measure density during plasma acceleration. As mentioned, these are merely some of numerous variety of ports which may be used. Various diagnostics related to the Z-pinch 100 may be designed to measure plasma flow profile and the stability of the plasma pinch, as well as the plasma equilibrium parameters. Those skilled in the art will readily appreciate a variety of ports which may be useful in order to obtain observation, measurement, and other kinds of information.

The Z-pinch 100, on one end, may comprise a capacitor bank 126 that provides potential difference between the inner 106 and outer 114 electrode. The capacitor bank may provide, for example, 17.5 kJ configured as a pulse-forming network. With this capability, a peak current of 150-200 kA may be provided, with a rise time of 25 μs, a flat-top of 35 μs, and a fall time of 40 μs.

In one implementation of the Z-pinch 100, the acceleration region 116 may be 1 m long, with a 20 cm diameter outer electrode 114 and a 10 cm diameter inner electrode 106. (Of course, these are merely exemplary dimensions, and the Z-pinch as a light source in some systems could be constructed on the order of centimeters or less—depending on the need of the system and the goals of the users of the Z-pinch).

Thus, neutral gas can be injected with fast gas puff valves (see FIGS. 2A-2E) into the midplane annulus of the coaxial Z-pinch 100, along the injection plane 112. The amount of injected neutral gas can be controlled by varying the plenum pressure in the puff valves. An electrical potential of about 5 to 9 kV can be applied to the acceleration region 116 to breakdown the neutral gas and thus ionize it (however, depending on the need, more or less potential can be applied, and thus these figures of 5 to 9 kV are merely exemplary and not limiting). The ionized gas, or plasma, can then be accelerated to a large axial velocity along the direction of the axis of symmetry 104.

Once the plasma exits the acceleration region 116, it can form a Z-pinch plasma column along the axis of symmetry 104 in the assembly region 118. The Z-pinch plasma can be 1 m long (roughly the length of the assembly region 118) and can be about 1 cm in radius. This process can then be repeated, as the magnetic field in the acceleration region 116 continues to accelerate plasma into the assembly region 118 to form a Z-pinch plasma, thus replacing old plasma as it exits the Z-pinch through an aperture 130. Inertia can maintain the flow of the plasma along the axis of symmetry 104, that is, inertia generated in the acceleration process can maintain the flow of the plasma through the entire assembly region 118. Also, various devices 132 may be coupled to the Z-pinch 100 in order to collect the EUV light emitted from a given plasma pinch, and provide it to other devices and apparatuses, such as optical devices and masks, which may use the EUV light in integrated circuit manufacture.

During the quiescent period (see below for more details), when the plasma has aligned along the axis of symmetry 104, the plasma velocity may be about $10^5$ km/s (10 cm per 1 μs), which means that it can transit the length of the assembly region 118 every 10 μs, if the length of the assembly region 118 is 1 meter—as discussed above (although, other commercially viable dimensions may also be used, as will be readily recognized by those skilled in the art). Once the plasma has gone through this transition, it can be replaced by new plasma via a valve (for example, see valve 206 in FIG. 2A)—especially if impurities contaminate the plasma, or if the plasma is lost somehow.

In one aspect of the disclosed subject matter, the voltage is applied and drives the current which accelerates and compresses the plasma. The current depletes the stored energy in the aforementioned capacitors. The voltage can remain connected to the system. After the quiescent period, the plasma may become unstable and end the relevant portion of the pulse (or pinch). Additional currents may flow through the remnant plasma, but this may not produce a useful pinch. Finally, when the capacitor energy is too low, all currents cease. The switch used to connect the capacitors to the electrodes may use a current to maintain connectivity. At this point the switch may open. To begin the next pulse (or second pinch), the capacitors can be recharged, neutral gas can be injected, the voltage can be applied, and on.

An aperture to collect EUV light emitted by the plasma could be arranged either axially or radially. In FIG. 1, the aperture 130 is arranged axially along the axis of symmetry 104, but it could just as easily be located radially at the location of one of the ports 122. The emitted light could be emitted from the full volume of the plasma during the quiescent period and it could be collected during this period, which may extend to 40 μs or more. The collected light, in turn, could be applied to condenser optics in order to be used in the manufacture of integrated circuits (that is, the light could be applied to silicon or other wafers).

As indicated already, the Z-pinch may provide various port and measuring mechanisms. For example, the electron density in the Z-pinch 100 can be measured with a two-chord, HeNe interferometer with a heterodyne, quadrature detector. One chord can traverse the plasma along a diameter, and a second cord can be parallel to and 2 cm above the first chord. The average plasma density in the Z-pinch 100 can then be determined from the line-integrated densities from the two chords to be approximately $2\times10^{22}$ $m^{-3}$.

The magnetic field in the Z-pinch 100 can be measured with an azimuthal array of eight surface-mounted magnetic probes located in the outer electrode 114. As mentioned, the plasma pinch radius might be approximately 1 cm, corresponding to a magnetic field at an edge of the Z-pinch plasma of 1 to 2 T during the lifetime of the Z-pinch plasma. Data from these probes can be Fourier analyzed to determine the time-dependent evolution of the low order azimuthal modes (e.g. m=1, 2, 3).

Figure 1B:
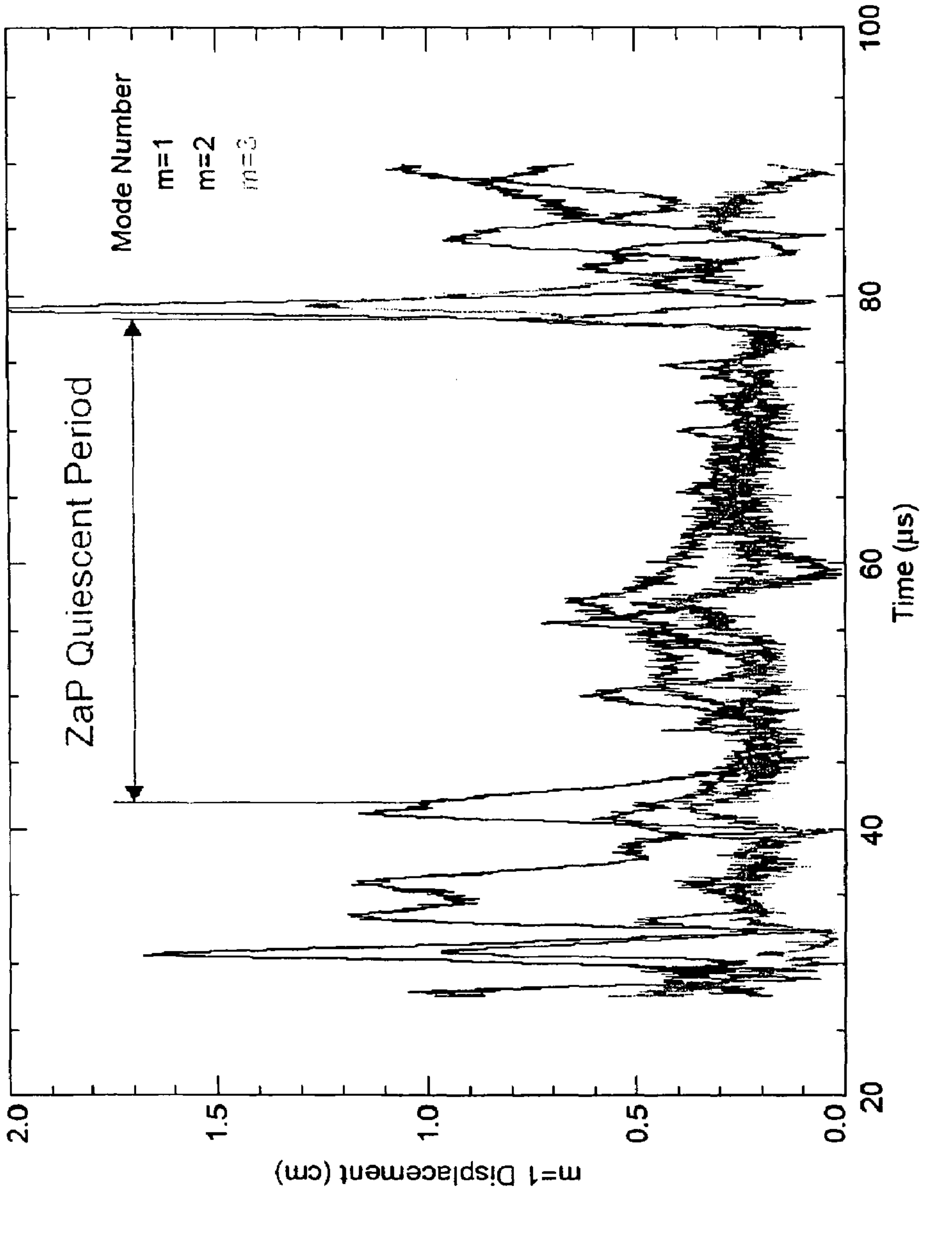
FIG. 1B illustrates the evolution of Fourier modes of the displacement of pinch current set at a predetermined point in a Z-pinch, where large magnetic fluctuations occur during pinch assembly, after which the amplitude and frequency of the magnetic fluctuations diminish.

FIG. 1B shows the evolution of the m=1, 2, and 3 Fourier modes of the displacement of pinch current set at the z=0 line 132 of FIG. 1A. Large magnetic fluctuations occur during pinch assembly, after which the amplitude and frequency of the magnetic fluctuations diminish. This stable behavior continues for 35 μs to 45 μs, and defines the quiescent period. At the end of the quiescent period, fluctuation levels again change character, increase in magnitude and frequency, and remain until the end of the plasma pulse.

Figure 1C:
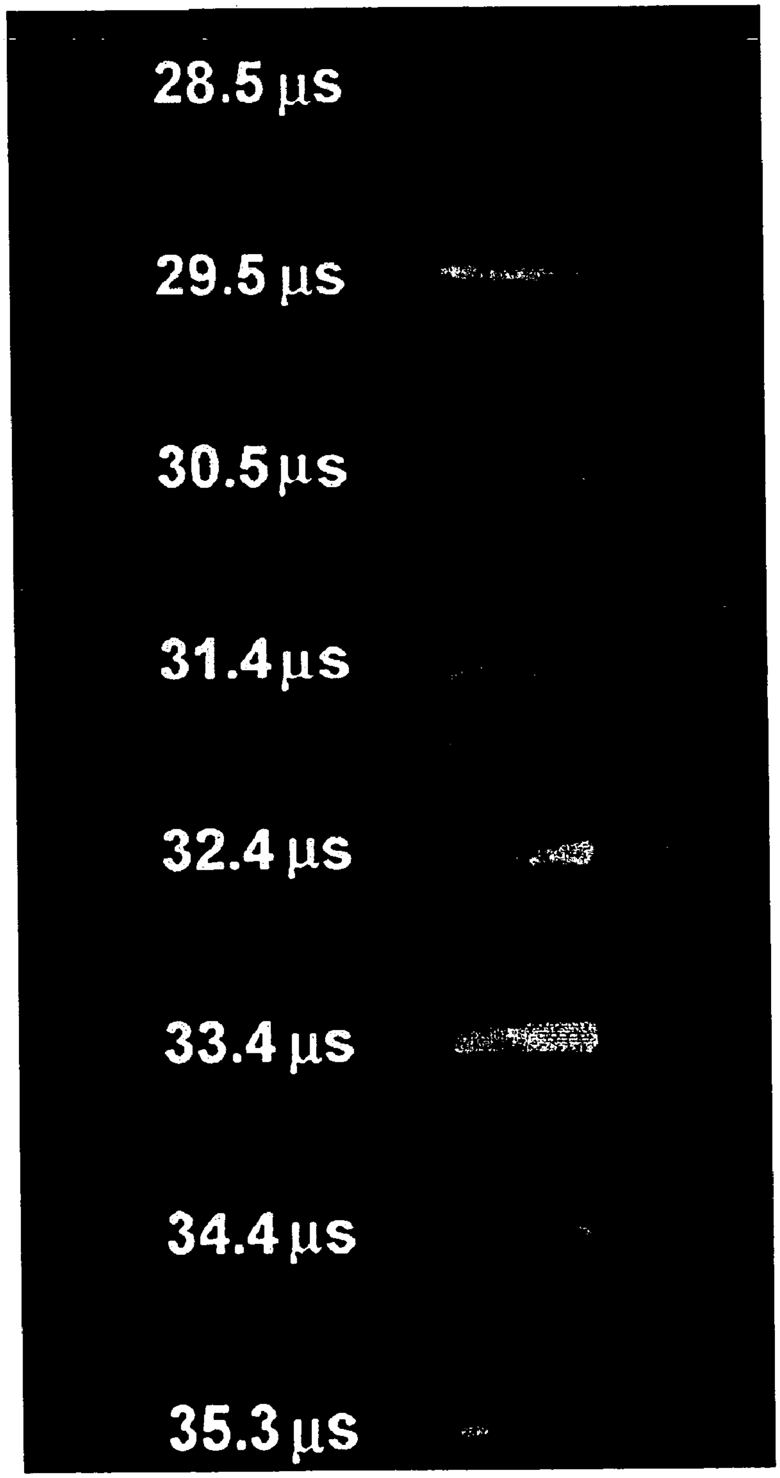
FIG. 1C illustrates, at various temporal intervals, plasma in its stable state, as can be seen through a typical port of the Z-pinch.

FIG. 1C, in fact, illustrates the plasma in its stable state, as can be seen through one of the ports, discussed above, in the Z-pinch 100. In FIG. 1C, optical emission images of the plasma are shown, obtained with a fast framing camera equipped with a notch pass filter which passes light with wavelengths between 500 and 600 nm. The images, taken at intervals of 28.5 μs, 29.5 μs, 30.5 μs, 31.4 μs, 32.4 μs, 33.4 μs, 34.4 μs, and 35.3 μs, clearly show the stability of the plasma for an extended period of time.

Notably, data from other diagnostics are consistent with this description of the plasma behavior. The timing of the stable period shown in FIG. 1C corresponds to the stable time shown in the displacement mode data in FIG. 1B.

One of the results observed from the plasma seen in FIG. 1C is the brightness of the light from the plasma pinch. This unexpected result, a function of the temporal length of the plasma pinch formed by sheared flow of the plasma, plasma density, and the plasma temperature, leads to the plasma pinch EUV light output being significant and efficient, and suitable for example, for EUV lithography.

Also, plasma flow velocity profiles can be determined by measuring the Doppler shift of plasma impurity lines using an imaging spectrometer with an intensified CCD camera (ICCD) operated with a 100 ns gate. The spectrometer images 20 spatial chords through the plasma pinch at an oblique angle to the plasma axis, providing a measurement of the axial velocity profile. The chord-integrated data can be deconvolved to determine the axial velocity profile. The velocity profile can be measured at one time during a pulse. The evolution of the velocity profile evolves from a large uniform flow during pinch assembly to one that is sheared (non-uniform) during the quiescent period. At the end of the quiescent period, the velocity quickly decays, resulting in a plasma profile that is low and uniform.

The theoretical growth time for a static Z-pinch is 21 ns for the measured experimental values and a mode with $ka=\pi$, where "k" is the axial wave number of the mode, and "a" is the plasma radius. The experimental results of this exemplary implementation show a stable period of approximately 40 μs, which is almost 2000 (two thousand) exponential growth times. The experimentally measured axial velocity shear exceeds the theoretically required shear threshold during the quiescent period and the shear is below the threshold outside of the quiescent period. The correlation of the experimental stability data with the plasma flow measurements is consistent with the sheared flow stabilization theory.

In another aspect of the disclosed subject matter, the power output by the Z-pinch is the product of the energy per plasma pulse and the duty cycle. The energy per pulse is expected to be proportional to the product of the plasma volume and the plasma lifetime. The ratio of the energy per pulse for a flow Z-pinch EUV source to that of a typical gas discharge-produced plasma (GDPP) source can be approximately $1\times10^5$. For example, the Z-pinch plasma may have a volume of 300 cc (cubic centimeters) and its lifetime may be 30 μs (microseconds), while the GDPP may have a volume of 1 cc and a lifetime of 0.1 μs. Thus, (300 cc*30 μs)÷(1 cc*0.1 μs)≈$1\times10^5$. In fact, a flow Z-pinch EUV source should produce much higher power even with a lower duty cycle than traditional mechanisms, such as the GDPP. The value may be higher than $1\times10^5$, and with a heavier gas like Xenon (Xe), the plasma lifetimes may be longer.

Aspects of Producing EUV Light Based on Sheared Plasma Flow

One of the goals of the Z-pinch 100 device depicted in FIG. 1A and measured in FIGS. 1B and 1C, is to use sheared plasma flow in order to stabilize an otherwise unstable plasma configuration. Stabilization of the plasma configuration can then be used to produce significant EUV light, which in turn might be useful in such technological fields as EUV lithography, as for example, in computer chip manufacture. One of the reasons EUV light generated by the Z-pinch 100 is especially useful in lithography is that it can produce enough power—on the order of 100 watts or more—which is useful in chip manufacture.

One aspect of "sheared" plasma flow is that such flow is non-uniform. As mentioned, quiescent plasma can be produced with such flow that lasts around 40 μs. This length of time is longer by a factor of 2000 over anything that has been produced in the art to date. Such prolonged maintenance of a plasma pinch and the associated EUV emission can be directly applied to such uses as lithography.

FIGS. 2A to 2E explain one way in which sheared plasma flow can be accomplished. Starting with FIG. 2A, the upper portion 108A and 110A (see FIG. 1A) of the acceleration region 116 and the assembly region 118, respectively, of a Z-pinch 200 are depicted. An inner electrode 202 is in a coaxial configuration with an outer electrode 204. As mentioned, one of these electrodes can be an anode and the other can be a cathode. A valve 206 is shown, which allows gas 208, for example, neutral gas, to be injected into the interstice 203 between the inner electrode 202 and the outer electrode 204. The gas 208 can the move across the line 212 demarcating the acceleration region 108A from the assembly region 110A, to eventually line up along the axis of symmetry 210 to form a Z-pinch plasma.

Figure 2A:
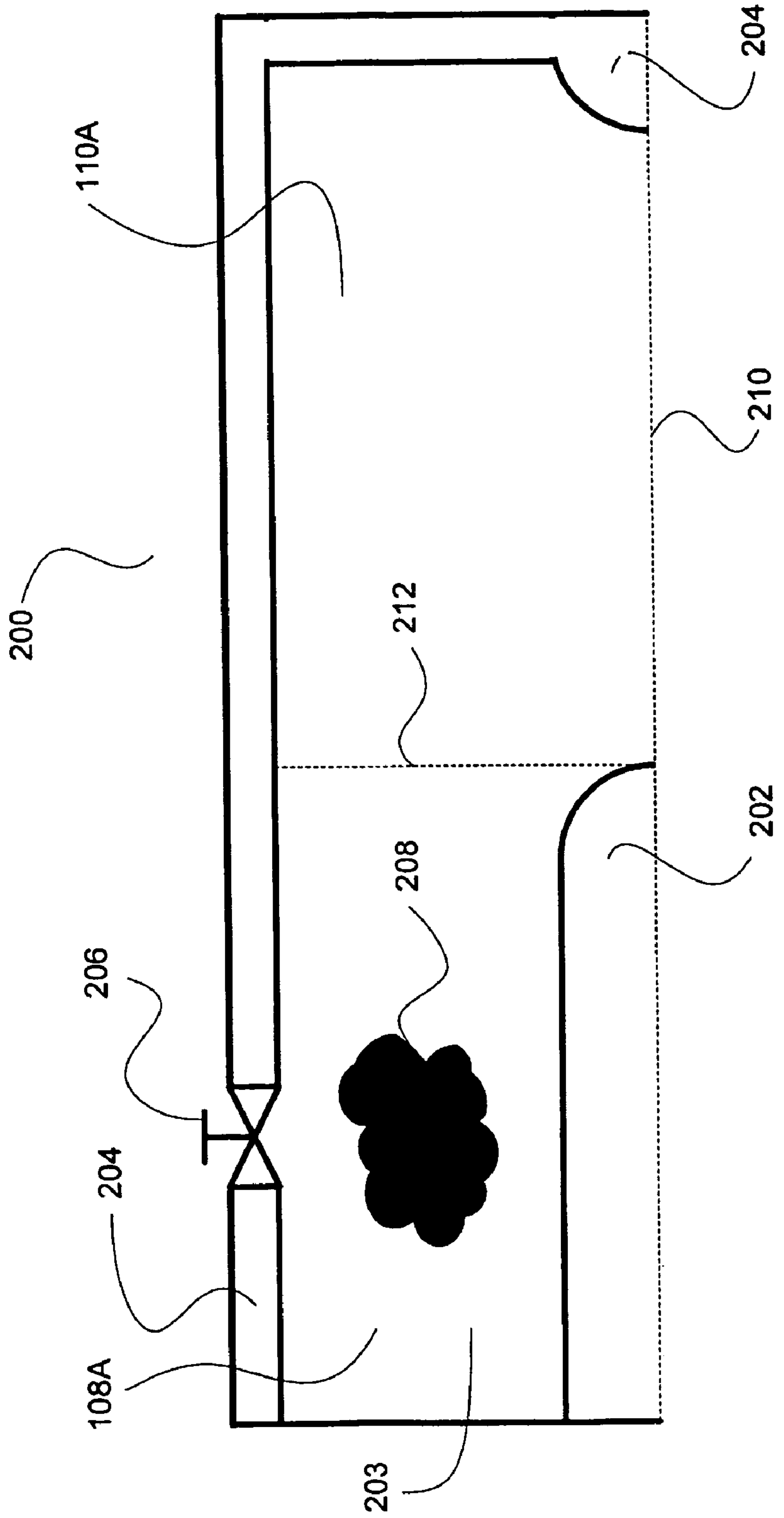
FIG. 2A illustrates an initial phase of sheared plasma flow production that will eventually lead to EUV production.
Figure 2B:
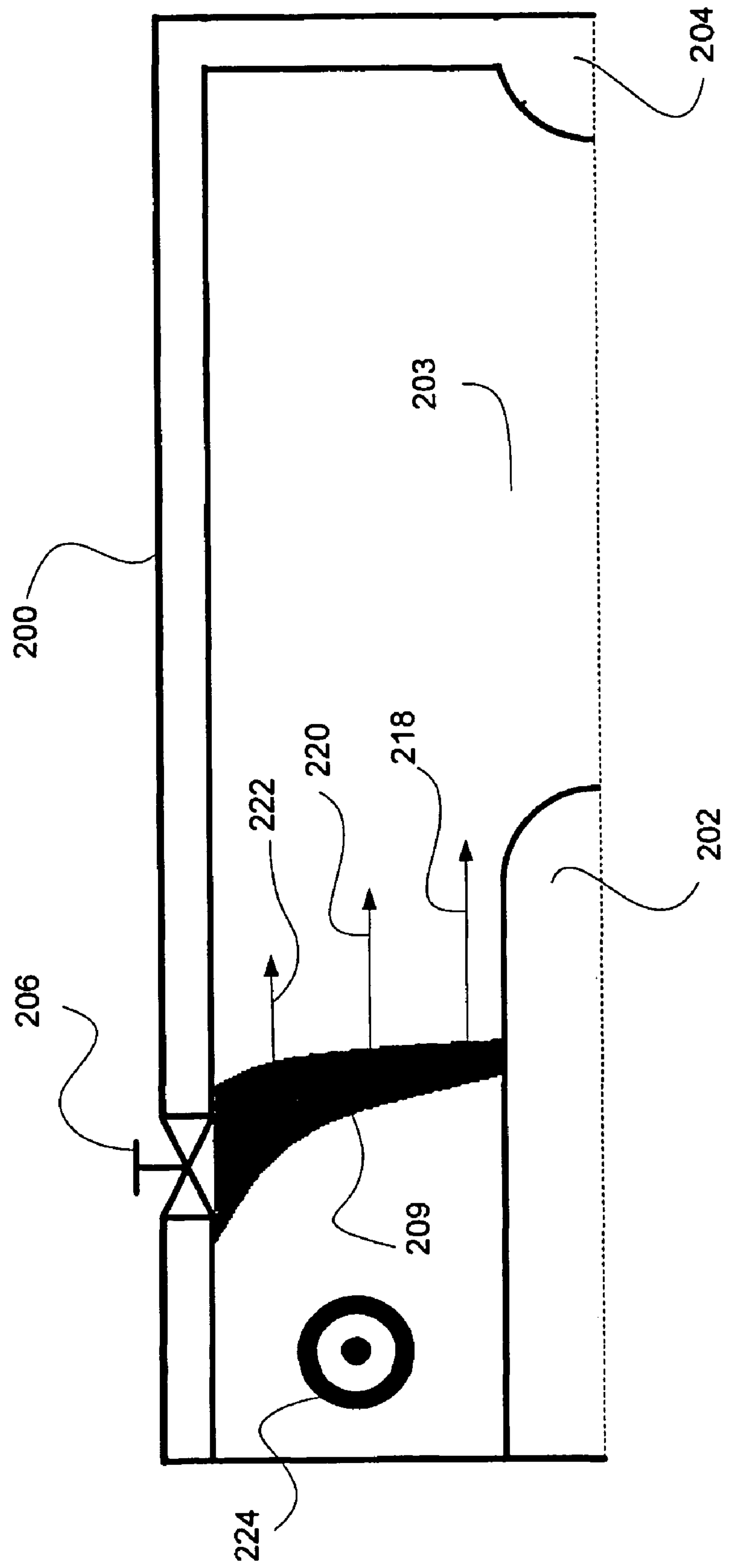
FIG. 2B illustrates what happens when a self-generated magnetic field interacts with the injected plasma, and the direction of the acceleration of the sheared plasma flow from an acceleration region to an assembly region.

Next, FIG. 2B depicts the beginning of sheared plasma flow. Once the gas 208 has been injected in the interstice 203, a voltage is applied to ionize the gas into a plasma 209. The plasma 209 conducts a current between the inner electrode 202 and the outer electrode 204 and this produces a magnetic field (B) 224 in the interstice 203 to the left of the plasma 209 shown in FIG. 2B. The current and the magnetic field interact to produce a Lorentz force which accelerates the plasma in the direction of the illustrated arrows 218, 220, and 222. The magnetic field and the current density have a radial dependence. The result is that the plasma 209 is accelerated non-uniformly, that is, in a sheared manner, as can be seen by the non-uniform width of the plasma 209. It should be noted, however, that an applied magnetic field could just as easily be added to improve the stability characteristics of the plasma. Various acceleration techniques are envisioned by the presently disclosed subject matter, none of which is dispositive but merely exemplary.

Figure 2C:
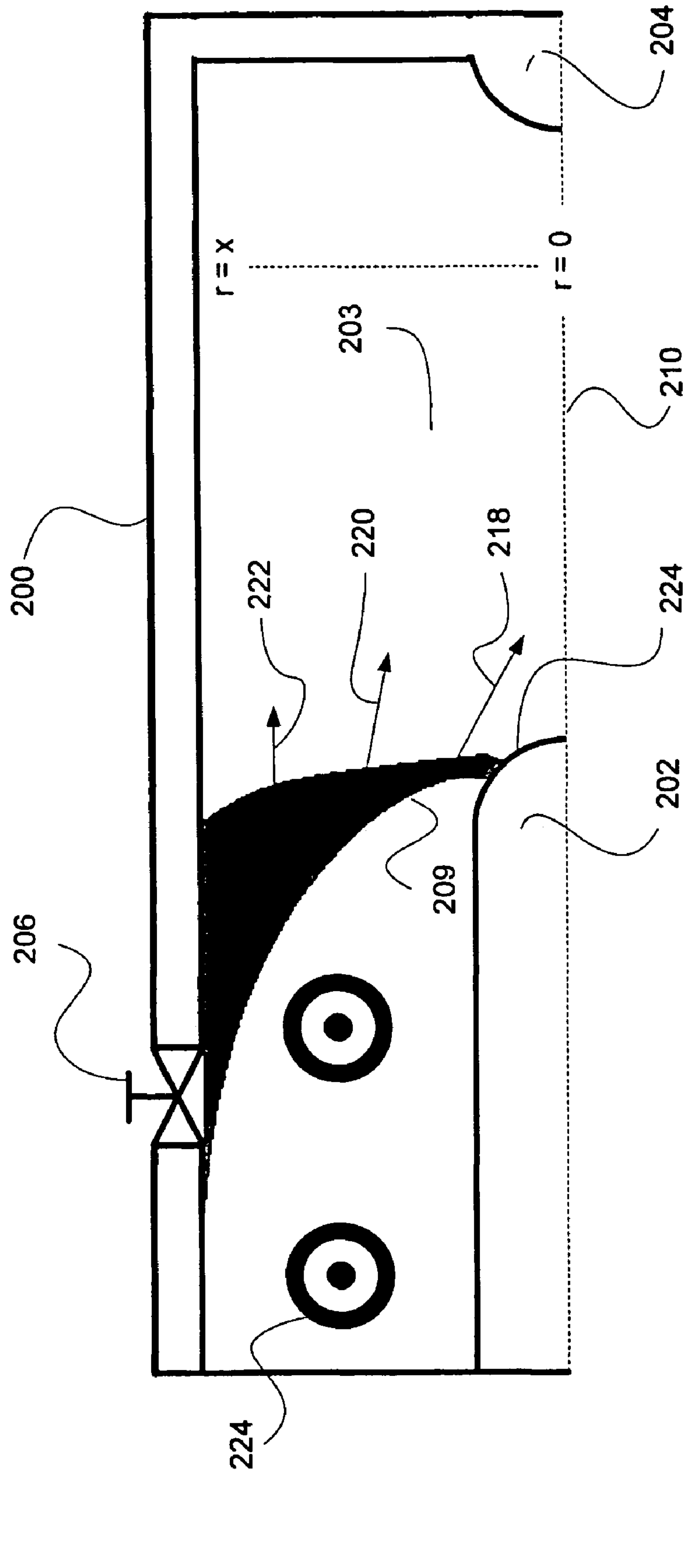
FIG. 2C illustrates the transition from the acceleration region to the assembly region, as the plasma is beginning to line up along the axis of symmetry in order to form a plasma pinch.

Specifically, with reference to FIG. 2C, the force on the plasma 209 is non-uniform. The force varies as $1/r^2$, where "r" is the radius of the interstice 203, beginning at the axis of symmetry, where r=0, and going up to the inner wall of the outer electrode 204, where r=x (some non-zero number). Thus, as can been seen via vector forces 218, 220, and 222, the force 218 nearest the axis of symmetry 210 is the strongest and the force 222 nearest the outer electrode 204 is the weakest (the length or magnitude of the vectors indicates force strength). This disparity of force strength causes the non-uniform or sheared flow of the plasma 209.

The shear that is generated due to the radially varying acceleration force, which varies as $1/r^2$, as stated above, tends to cause the plasma along the inner electrode 106 to accelerate faster than the plasma toward the outer electrode 114. The force is proportional to $B^2$, and B (the magnetic field) varies as 1/r. Moreover, in another aspect of the disclosed subject matter, the plasma flow can be monotonic, that is, it can have a single high flow region transitioning to a single low flow region—but this is not required. The shear also tends to satisfy the shear threshold for stability: $dVz/dr>0.1\ k\ Va$, where k is the axial wave number, dVz/dr is the radial shear of the axial velocity, and Va is the Alfven speed characteristic of the plasma.

Interestingly, the geometry of the electrodes also aids in sheared plasma 209 flow. For example, the inner electrode 202 is smooth 224 in such a way that it helps in the transition of the plasma 209 from its original starting place around the valve 206 towards the ending place around the axis of symmetry 210, along which it will eventually assemble.

Figure 2D:
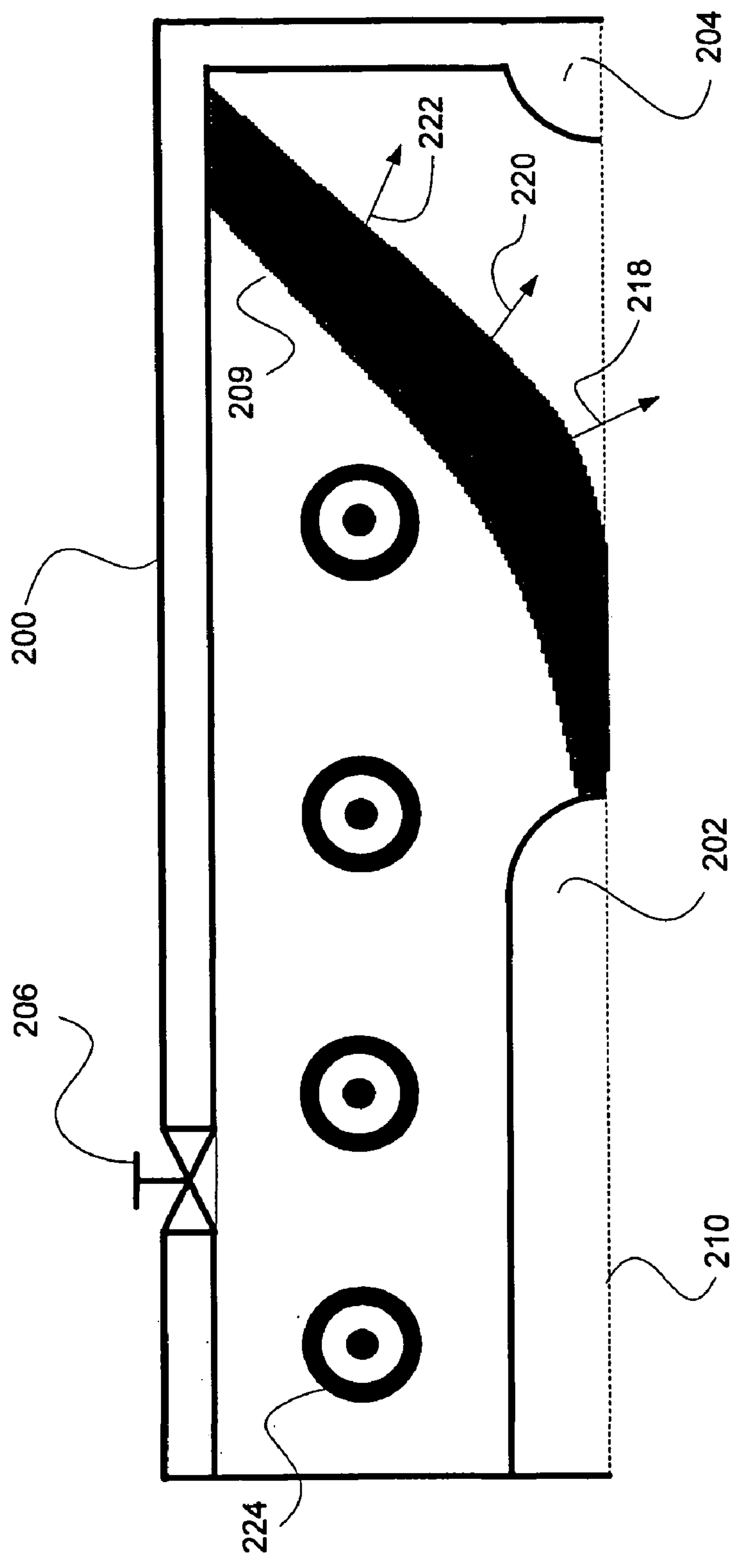
FIG. 2D illustrates the phase before the plasma aligns along the axis of symmetry and how the magnetic field pushes the plasma current sheet towards the pinch between two coaxially configured electrodes.

FIG. 2D illustrates the scenario where the stationary magnetic field 224 keeps pushing the plasma 209 towards the axis of symmetry 210 to form a Z-pinch plasma. The forces 218, 220, and 222 keep changing in magnitude and direction as the plasma 209 accelerates, from left to right, across the Z-pinch 200. This force variability causes sheared plasma 209 flow.

Figure 2E:
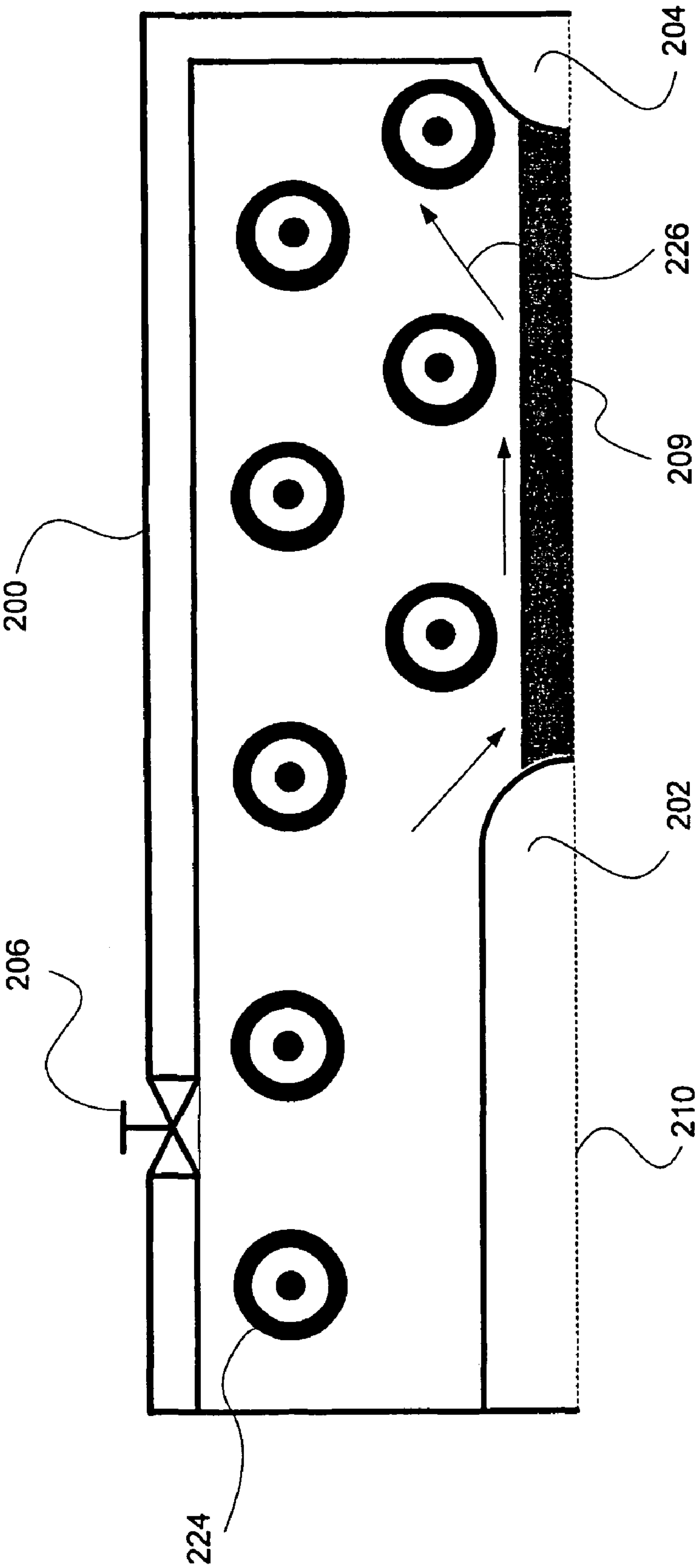
FIG. 2E illustrates how the sheared accelerated plasma aligns along the axis of symmetry to form a plasma pinch which can produce EUV light, where the plasma pinch that is formed is a column of plasma between an inner and outer electrode in an coaxial geometric relationship.

Finally, in FIG. 2E, a scenario is shown where the plasma 209 has settled down along the axis of symmetry 210. The stationary magnetic field 224 keeps the plasma 209 along the axis 210, as indicated by the depicted forces 226. As mentioned above, such plasma 209 pinches can be maintained on the order of 40 μs, which is at least 2000 times longer than anything hitherto predicted or accomplished. Once the plasma 209 pinch is sustained, EUV light is emitted from plasma 209. Depending of what type of plasma is used, different wavelengths of light will be produced. For example, if the desired wavelength is in the EUV range, such elements as Xenon, Tin, or Lithium can be used.

Figure 3:
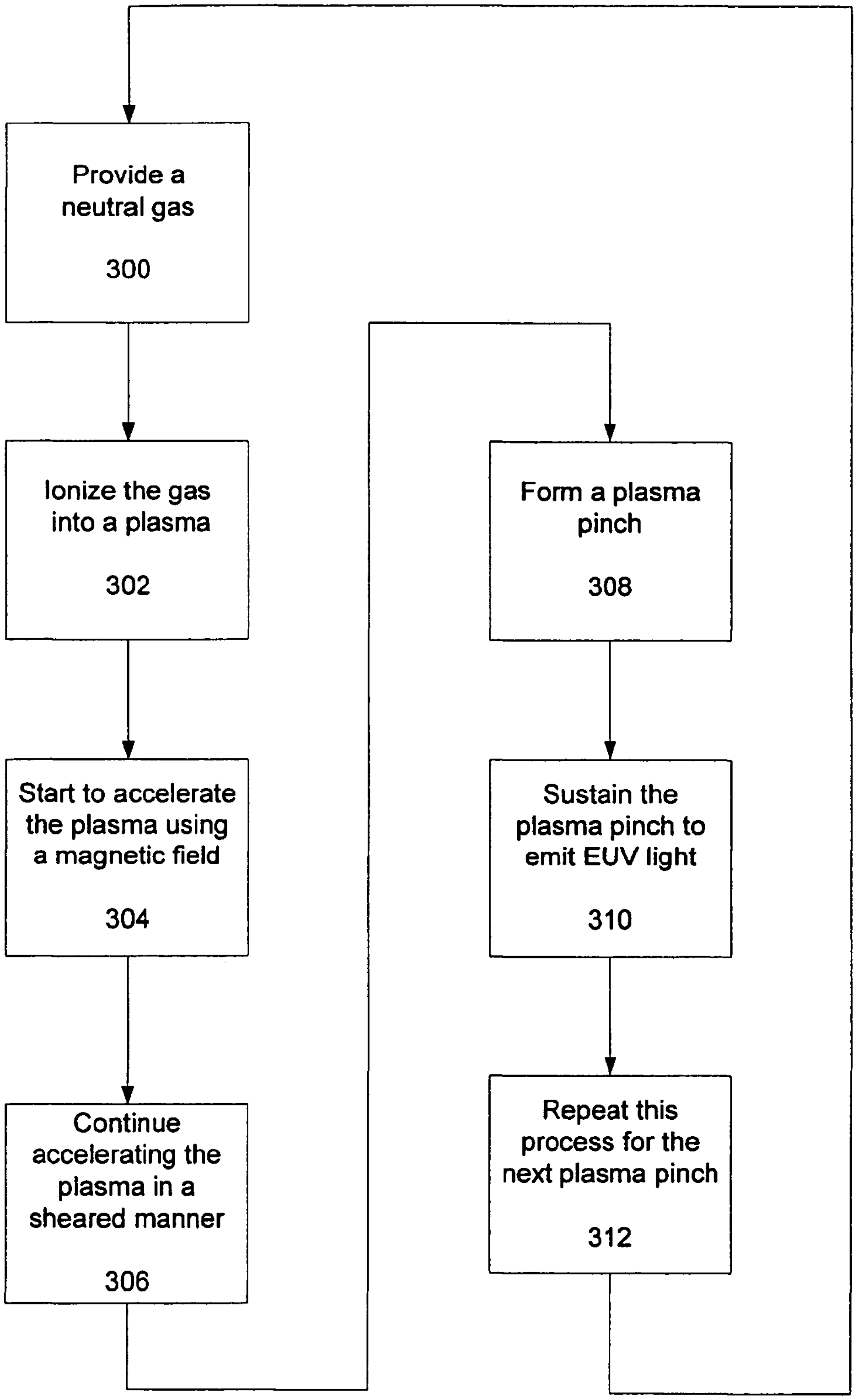
FIG. 3 illustrates in block diagram flow chart form exemplary steps in generating an EUV light output from a sheared plasma flow.

FIG. 3 shows a block flow chart of one typical implementation of the sheared flow plasma for producing EUV. At block 300, a neutral gas or seed plasma is provided. Then, at block 302, neutral gas is ionized into a plasma. Next, at block 304, the plasma is being accelerated using a magnetic field. The acceleration is performed in a sheared manner, as indicated at block 306. Once, the plasma is accelerated in a sheared manner, it is eventually formed into a plasma pinch, at block 308, between two electrodes. Finally, at block 310, the plasma pinch is sustained for some period of time, as discussed above, so as to cause the plasma to emit EUV light during at least a portion of the time the plasma pinch is formed. Of course, this process can be repeated with each new injection of plasma, as shown by block 312, which feeds back to block 300. The rate at which this process could be reproduced ranges on the order of minutes to microseconds. For example, for mere experimental and measurement purposes, it could be reproduced every couple of minutes. For chip-making purposes, it could be reproduced at the rate of several kilohertz. Moreover, the time-averaged power EUV light output could range from several watts to several hundred watts. In one aspect, suitable for chip manufacture, the power output by the Z-pinch plasma could be 110 watts at the intermediate focus. Moreover, the wavelength of EUV light, given, for example, Xenon, Tin, or Lithium, could be in the range of 10 to 17 nm, or, if such EUV light is sought for chip manufacture, it could be about 13.5 nm.

Aspects of a System for Using EUV Light

Lastly, given the above discussion of the type of devices that might be used for EUV emission, and the process of providing such emission, a system is herein disclosed for using such EUV emission in lithography.

Typical lithography, such as Deep Ultraviolet (DUV) lithography, which uses light with wavelengths in the 193 nm to 248 nm range, may comprise the following functional blocks: (1) light source; (2) reticle; (3) reticle stage; (4) projection optics; (5) wafer stage; (6) alignment system; and (7) focus system. Those skilled in the art will readily appreciate these blocks and any additional blocks required or desired in lithography. However, EUV lithography differs from DUV lithography in at least four respects: (1) EUV light source may be in the 13.5 nm range, not the 193 nm range; (2) reflective optics may be used instead of the predominantly refractive DUV optics; (3) reflective reticles may be used instead of transmitting DUV reticles; and (4) the EUV system may employ a vacuum environment instead of the nitrogen-purged environment for DUV.

Figure 4:
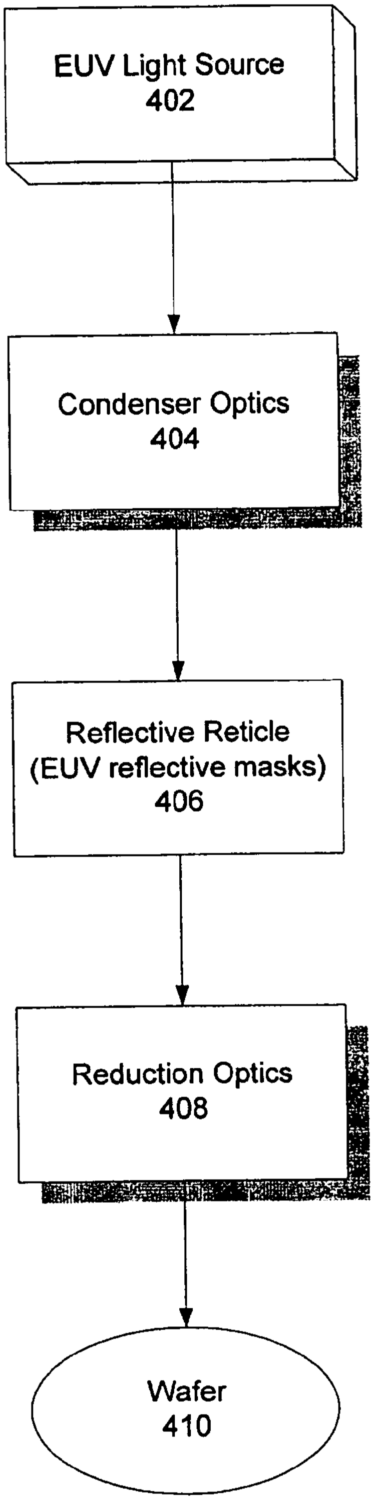
FIG. 4 illustrates an exemplary EUV lithography system, where the device of FIG. 1 can be implemented in such a system which may be configured to integrated circuit manufacture.

FIG. 4 illustrates in block format one EUV system that may be employed. At block 402, an EUV light source is provided. The light source may be produced by the device discussed with reference to FIG. 1A and the process discussed with reference to FIG. 2A-2E. Once sheared plasma flow emits EUV light, that light can then be condensed.

Thus, at block 404, condenser optics are employed, which may consist of multilayered coated collector and grazing incidence optics which collect and shape an EUV beam in order to illuminate a reflective mask or reticle. Thus, at block 408, reflective reticles are provided. In such a set-up, a low-expansion reflective reticle clamped to a scanning reticle stage moves a mask across an illumination beam, and a reflective optical system with aspheric components produces an x times reduction of the mask image, as indicated at block 408. Finally, at block 410, the scanning wafer stage containing a semiconductor substrate coated with EUV-sensitive photoresist can scan the wafer across the EUV beam in synchronism with the scanning reticle stage.

Many different systems could be implemented with the sheared plasma flow emitting EUV source. The system discussed herein is merely exemplary and therefore not limiting in any manner. As mentioned already, an EUV system will differ from a DUV system which may be employed currently in the art, based on the shorter wavelengths employed by the EUV system, the importance of reflective optics and reticles (in contrast to refractive ones used in DUV), and the importance of a vacuum environment to address impurities and absorption issues.

As mentioned above, the EUV light source can be used in a lithography system. However, this is merely one exemplary use of the light source. It can also be used in a sterilization system, a nanoprobe fabrication system, in high resolution microscopy and holography, and so on. Those skilled in the art will readily appreciate the numerous applications of such an EUV light source.

While the present disclosure has been described in connection with the preferred aspects, as illustrated in the various figures, it is understood that other similar aspects may be used or modifications and additions may be made to the described aspects for performing the same function of the present disclosure without deviating therefrom. For example, in various aspects of the disclosure, a sheared flow plasma pinch was discussed, where such a plasma pinch was configured to emit EUV light, which may be useful, for example, in lithography. However, other equivalent mechanisms to these described aspects are also contemplated by the teachings herein. Therefore, the present disclosure should not be limited to any single aspect, but rather construed in breadth and scope in accordance with the appended claims.

What is claimed:

1. A method for producing extreme ultraviolet (EUV) light, comprising:
- providing a plasma;
- accelerating the plasma to produce a sheared plasma flow;
- forming a plasma pinch from the accelerated plasma; and
- sustaining the plasma pinch for a period of time so as to allow the plasma to emit EUV light during at least a portion of said period of time.

2. The method according to claim 1, further comprising replacing the plasma after the plasma pinch has been sustained and providing a new plasma used in EUV light emission.

3. The method according to claim 1, wherein the plasma is accelerated at a rate to satisfy a stability threshold.

4. The method according to claim 1, wherein the plasma comprises Xenon.

5. The method according to claim 1, wherein the plasma comprises Tin.

6. The method according to claim 1, wherein the plasma comprises Lithium.

7. The method according to claim 1, wherein the plasma comprises ionizable gas configured to emit EUV light.

8. The method according to claim 1, further comprising applying a voltage in the range of about 5 kV to 9 kV to the plasma before it is accelerated.

9. The method according to claim 1, wherein the period of time is at least one of (a) about 20 microseconds to 40 microseconds and (b) at least 40 microseconds.

10. The method according to claim 1, wherein the plasma pinch is formed at a rate of about 1 kilohertz.

11. The method according to claim 1, wherein the plasma pinch is formed at a rate of about 10 to 100 hertz.

12. The method according to claim 1, wherein the plasma pinch produces at least 100 watts of EUV power at an intermediate focus.

13. The method according to claim 1, wherein the EUV light has a wavelength in the range of about 10 to 17 nanometers.

14. An apparatus for producing extreme ultraviolet (EUV) light, comprising:
- a first electrode;
- a second electrode, wherein the second electrode is configured coaxially with respect to the first electrode, such that a pinch is formed between one end of the first electrode and an adjacent region of second electrode, wherein the pinch is configured to receive a sheared flow of a plasma;
- an injection port configured for injection of at least one of (a) gas and (b) plasma into a region formed between the first electrode and the second electrode; and
- an access port configured for providing access to EUV light emanating from the plasma formed in the pinch.

15. The apparatus according to claim 14, wherein one of the first electrode comprises one of (a) a cathode and (b) an anode.

16. The apparatus according to claim 14, wherein the first electrode is substantially curved along one end, thereby permitting a smooth transition of the plasma from the region to the pinch.

17. The apparatus according to claim 14, wherein the second electrode comprises one of (a) a cathode and (b) an anode.

18. An lithography system for producing extreme ultraviolet (EUV) light, comprising:
- a plasma source for emitting EUV light, wherein the plasma source generates the EUV light using sheared flow stabilized plasma;
- a mask, wherein the plasma source is directed at the mask; and
- a focusing apparatus for controlling the EUV light emanating from the plasma source and passing through at least one aperture of the mask.

19. The system according to claim 18, wherein the focusing apparatus comprises a reflective optic configured to point the EUV light at a substrate.

20. The system according to claim 18, wherein at least part of the system is encapsulated in a vacuum.

* * * * *